United States Patent
Li et al.

(10) Patent No.: US 12,312,311 B1
(45) Date of Patent: May 27, 2025

(54) ANTHRACENE-BASED COMPOUND, AND PREPARATION METHOD THEREFOR AND USE THEREOF AS SOLAR THERMAL FUEL

(71) Applicant: TAIYUAN UNIVERSITY OF TECHNOLOGY, Taiyuan (CN)

(72) Inventors: Wenying Li, Taiyuan (CN); Xingtang Xu, Taiyuan (CN); Wenjing Chen, Taiyuan (CN); Chonghua Li, Taiyuan (CN); Jie Feng, Taiyuan (CN)

(73) Assignee: TAIYUAN UNIVERSITY OF TECHNOLOGY, Taiyuan (CN)

( * ) Notice: Subject to any disclaimer, the term of this patent is extended or adjusted under 35 U.S.C. 154(b) by 0 days.

(21) Appl. No.: 19/023,407

(22) Filed: Jan. 16, 2025

Related U.S. Application Data (63) Continuation of application No. PCT/CN2024/119614, filed on Sep. 19, 2024.

(30) Foreign Application Priority Data

Sep. 5, 2024 (CN) .......................... 202411244270.7

(51) Int. Cl.
C07C 69/675 (2006.01)
C07C 15/28 (2006.01)
C07C 69/40 (2006.01)

(52) U.S. Cl.
CPC ............ C07C 69/675 (2013.01); C07C 15/28 (2013.01); C07C 69/40 (2013.01)

(58) Field of Classification Search
CPC ....... C07C 69/40; C07C 69/675; C07C 15/28; C07C 67/08
See application file for complete search history.

(56) References Cited

FOREIGN PATENT DOCUMENTS

| CN | 103183971 A | 7/2013 |
|---|---|---|
| CN | 115141077 B | 9/2023 |

OTHER PUBLICATIONS

Li, W-Y., et al., Coal-based solar thermal fuels: A perspective on clean utilization of coal tar, Chemical Engineering and Processing—Process intensification, Sep. 3, 2024 (online), vol. 205, No. 109976, pp. 1-7 (Year: 2024).*

(Continued)

Primary Examiner — Yate' K Cutliff
(74) Attorney, Agent, or Firm — Bayramoglu Law Offices LLC (57) ABSTRACT

An anthracene-based compound, and a preparation method therefor and use thereof as a solar thermal fuel are provided. The anthracene-based compound according to the present invention can be converted into a dimer under 365 nm ultraviolet irradiation and store light energy into chemical energy, and can be subjected to a depolymerization reaction under 254 nm ultraviolet irradiation and release heat. That is, the anthracene-based solar thermal fuel can store or release photo-thermal energy through a reversible photodimerization/depolymerization reaction. In addition, the anthracene-based compound has the unique advantage of photoinduced reversible solid-to-liquid transition, which can achieve the simultaneous storage of photon energy and phase transition energy. The anthracene-based compound has a storage energy density of approximately 65 KJ/mol and a storage half-life of up to 60 days.

20 Claims, 10 Drawing Sheets

(56) References Cited

OTHER PUBLICATIONS

Wen-Ying Li, et al., Coal-based solar thermal fuels: A novel perspective on clean utilization of coal tar, Chemical Engineering and Processing—Process Intensification, 2024, pp. 1-7, vol. 205 No. 109976.

Gaurab Ganguly, et al., Designing Efficient Solar-Thermal Fuels with [n.n](9, 10)Anthracene Cyclophanes: A Theoretical Perspective, the Journal of Physical Chemistry Letters, 2018, pp. 328-334, vol. 9.

Anders Lennartson, et al., Designing photoswitches for molecular solar thermal energy storage, Tetrahedron Letters, 2015, pp. 1457-1465, vol. 56.

* cited by examiner

ANTHRACENE-BASED COMPOUND, AND PREPARATION METHOD THEREFOR AND USE THEREOF AS SOLAR THERMAL FUEL

CROSS REFERENCE TO THE RELATED APPLICATIONS

This application is a continuation application of International Application No. PCT/CN2024/119614, filed on Sep. 19, 2024, which is based upon and claims priority to Chinese Patent Application No. 202411244270.7, filed on Sep. 5, 2024, the entire contents of which are incorporated herein by reference.

TECHNICAL FIELD

The present invention relates to the field of energy and chemicals industry, and in particular, to an anthracene-based compound, and a preparation method therefor and use thereof as a solar thermal fuel.

BACKGROUND

Anthracene, a polycyclic aromatic hydrocarbon containing three rings, is widely used in chemical production. In industry, anthracene is generally oxidized first and then is subjected to nitration and sulfonation to provide intermediates for fields such as dyes, medicines, and optoelectronic materials. The coal tar has a high content of anthracene. Chinese patent CN115141077B provides a method for separating anthracene from coal tar, which is simple in operation, mild in reaction conditions, and low in cost. In addition, anthracene has the advantages of controllable luminescence, easy energy and charge transfer, and unique photo- and thermal-reversible dimerization. However, the current preparation method for an anthracene-based compound is relatively complex, and there are few reports on the development of an anthracene-based solar thermal fuel based on photodimerization/depolymerization reactions. The solar thermal fuel is a molecular photoswitch that achieves light energy storage and thermal energy release based on the reversible transformation of molecular spatial configuration. The utilization process of the solar thermal fuel is cyclically stable without any gas and pollutant emissions. The anthracene-based compound exhibits a relatively low electronic energy gap due to having an extended aromatic x system, and is easy to form dimers. The dimers can quickly dissociate under light conditions. Therefore, the preparation of a novel anthracene-based compound and the exploration of the anthracene-based compound as a solar thermal fuel have an important application value in broadening the application ways of polycyclic aromatic hydrocarbon anthracene.

SUMMARY

An objective of the present invention is to provide an anthracene-based compound, and a preparation method therefor and use thereof as a solar thermal fuel.

To achieve the above objective, the present invention provides the following technical solutions.

The present invention provides an anthracene-based compound, which has a structure represented by formula 1:

formula 1 in formula 1, n=10 to 16.

Preferably, n=10, 13, or 16.

The present invention provides a preparation method for the anthracene-based compound according to the foregoing technical solution, which includes the following steps:

mixing anthracene, N-methylformanilide, phosphorus oxychloride, and a first solvent for a formylation-condensation reaction to obtain 9-anthracenecarboxaldehyde;

mixing the 9-anthracenecarboxaldehyde, sodium borohydride, and a second solvent for a reduction reaction to obtain 9-anthracenemethanol;

mixing the 9-anthracenemethanol, succinic anhydride, 4-dimethylaminopyridine, and a third solvent for a substitution reaction to obtain 4-(anthracene-9-ylmethoxy)-4-oxobutyric acid; and mixing the 4-(anthracene-9-ylmethoxy)-4-oxobutyric acid, 1-ethyl(3-dimethylaminopropyl)-3-carbodiimide hydrochloride, 4-dimethylaminopyridine, a long-chain fatty alcohol, and a fourth solvent for an esterification reaction to obtain the anthracene-based compound;

wherein the long-chain fatty alcohol has 12-18 carbon atoms.

Preferably, the anthracene is obtained from coal tar.

Preferably, a molar ratio of the anthracene to the N-methylformanilide to the phosphorus oxychloride is 1:2:2 to 1:4:4; a volume ratio of the N-methylformanilide to the first solvent is 10:1 to 5:1; and the formylation-condensation reaction is performed at a temperature of 90-100° C. for 2-8 h.

Preferably, a molar ratio of the 9-anthracenecarboxaldehyde to the sodium borohydride is 1:2 to 1:3; and the reduction reaction is performed at a temperature of 25° C. for 4-8 h.

Preferably, the third solvent comprises dichloromethane and pyridine; and a volume ratio of the dichloromethane to the pyridine is 1:1 to 3:1.

Preferably, a molar ratio of the 9-anthracenemethanol to the succinic anhydride to the 4-dimethylaminopyridine is 1:1:4 to 1:2:6; and the substitution reaction is performed at a temperature of 25° cfor 24-48 h.

Preferably, a molar ratio of the 4-(anthracene-9-ylmethoxy)-4-oxobutyric acid to the 1-ethyl(3-dimethylaminopropyl)-3-carbodiimide hydrochloride to the 4-dimethylaminopyridine to the long-chain fatty alcohol is 1:4:2:1 to 1:6:5:3; and the esterification reaction is performed at a temperature of 25° C. for 24-48 h.

The present invention provides use of the anthracene-based compound according to the foregoing technical solution or an anthracene-based compound prepared by the preparation method according to the foregoing technical solution as a solar thermal fuel.

The present invention provides an anthracene-based compound. The anthracene-based compound can be subjected to a photodimerization reaction under the ultraviolet irradiation with a specific wavelength to store photo-thermal energy and subjected to a photodepolymerization reaction under the ultraviolet irradiation with another wavelength to release heat. That is, this anthracene-based compound can be effectively subjected to a reversible photodimerization/depolymerization reaction to store or release photo-thermal energy, and has the unique advantage of photoinduced reversible solid-to-liquid transition. In addition, this anthracene-based compound has a high storage energy density (65 KJ/mol) and a long storage half-life (3 days), and can achieve simultaneous storage and utilization of photon energy and phase transition energy, which effectively improves the storage performance of the solar thermal fuel, and has a stable cycle in the utilization process without release of any greenhouse gas.

The present invention prepares an anthracene-based compound by using reversible photodimerization/depolymerization reaction of anthracene through the formylation-condensation reaction, the substitution reaction, and the esterification reaction. The prepared anthracene-based compound can be subjected to photodimerization under 365 nm ultraviolet irradiation accompanied by solid-liquid phase transition to simultaneously store photon energy and phase transition energy, and subjected to depolymerization under 254 nm ultraviolet irradiation accompanied by liquid-solid phase transition to simultaneously release the stored light energy and phase transition energy in the form of thermal energy.

The raw material anthracene adopted by the present invention for the preparation is commercially available or is a coal tar separation product, and the use of the anthracene-based compound as the solar thermal fuel can not only broaden the diversified utilization of the anthracene-based compound, but also further enrich the molecular system of the solar thermal fuel.

The anthracene-based compound according to the present invention is simple in synthesis process, high in yield, easy to produce in mass, stable in circulation, environment-friendly in utilization process, and capable of improving the clean utilization level of coal tar.

DETAILED DESCRIPTION OF THE EMBODIMENTS

The present invention provides an anthracene-based compound, which has a structure represented by formula 1:

formula 1 in formula 1, n=10 to 16.

In the present invention, n=10, 13, or 16.

Figure 1:
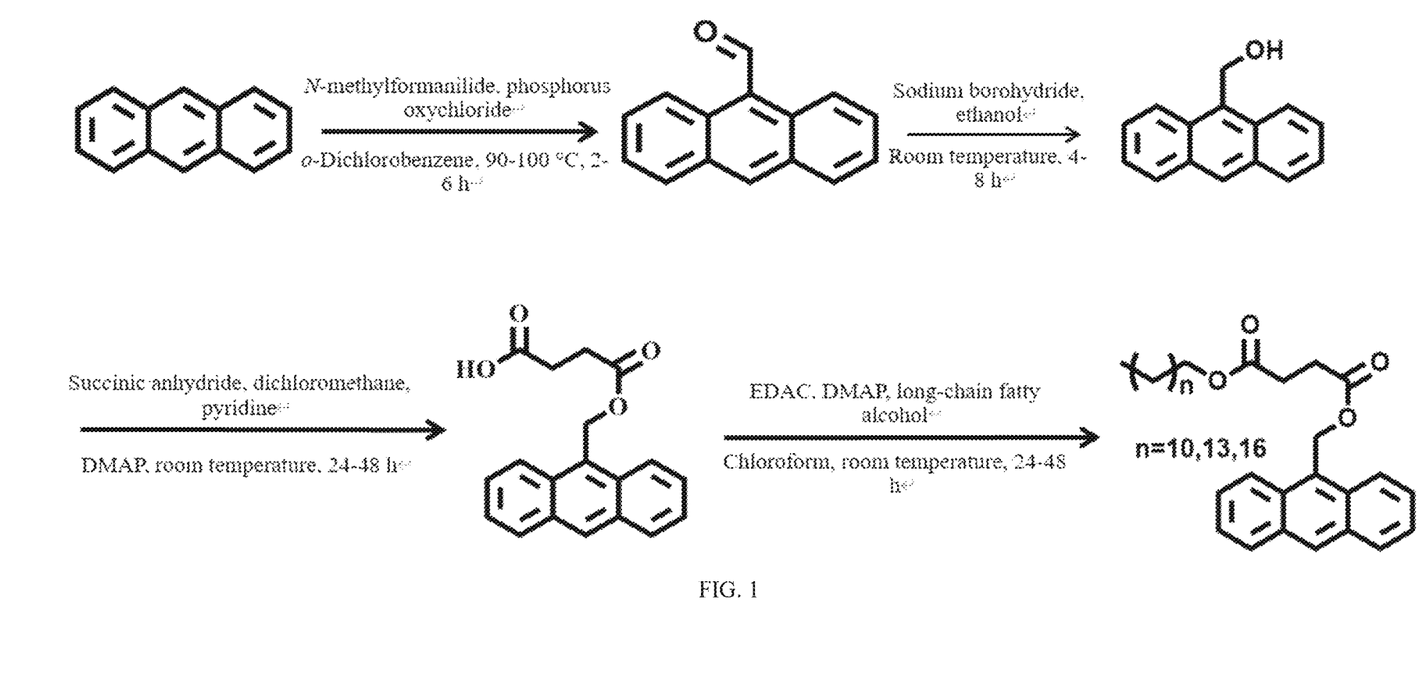
FIG. 1 is a synthetic route diagram of an anthracene-based compound according to the present invention.
Figure 2A:
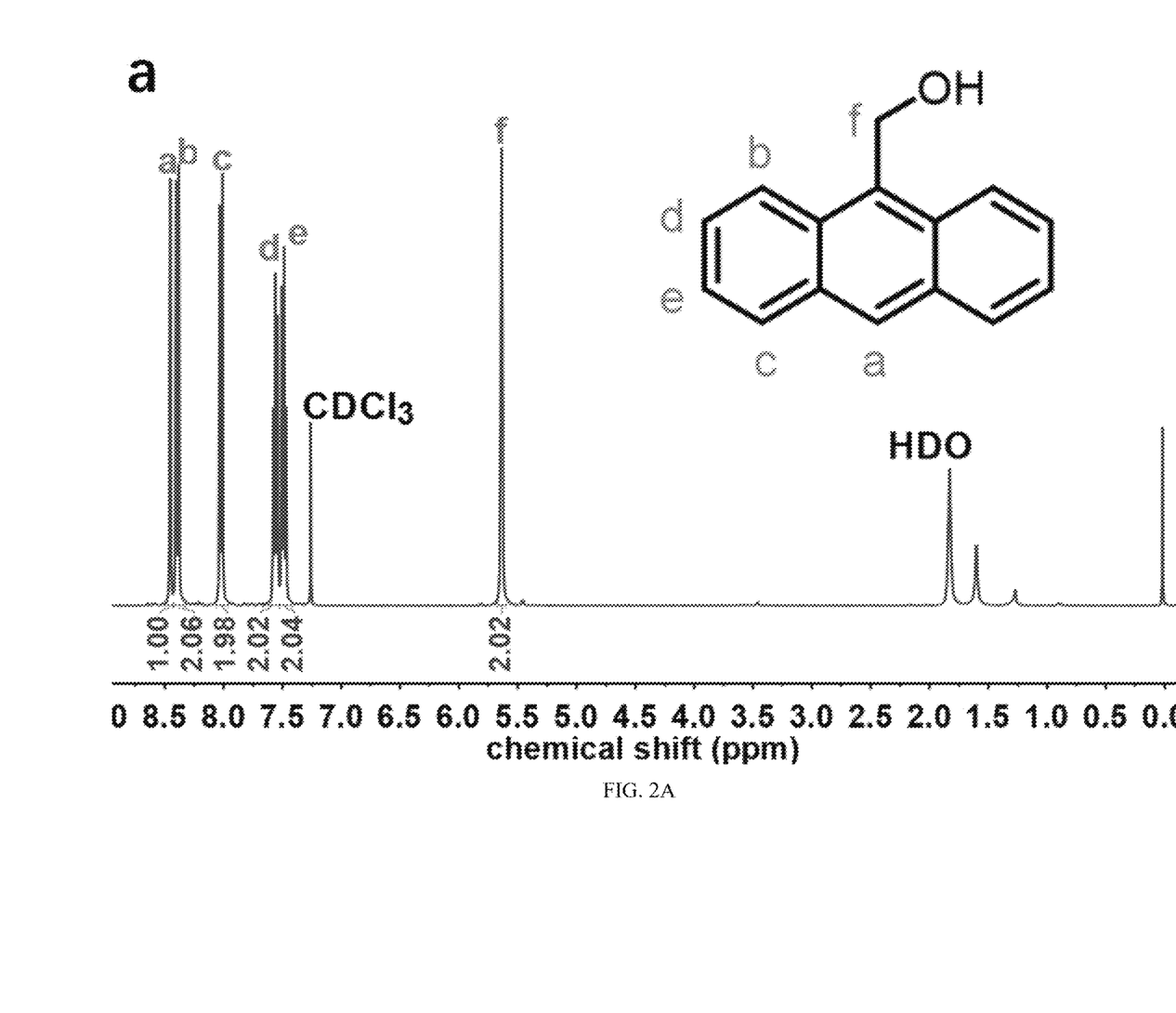
FIGS. 2A-2D are proton nuclear magnetic resonance (NMR) spectrums (deuterated chloroform) of 9-anthracenemethanol (FIG. 2A), the intermediate 4-(anthracen-9-ylmethoxy)-4-oxobutanoic acid (FIG. 2B) and the anthracene-based compound (FIG. 2C) and a mass spectrum of the anthracene-based compound (FIG. 2D) prepared in Example 1.
Figure 2B:
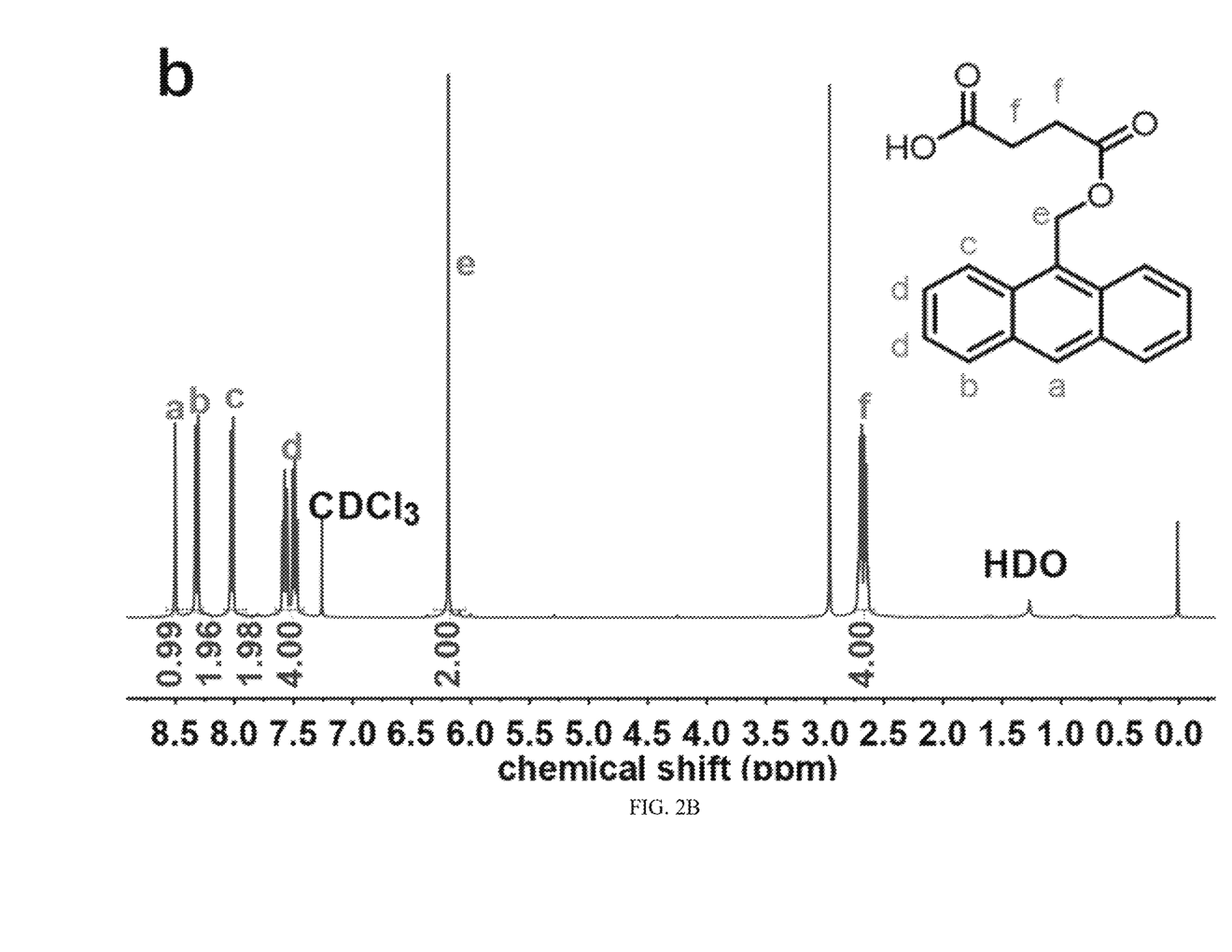
Figure 2C:
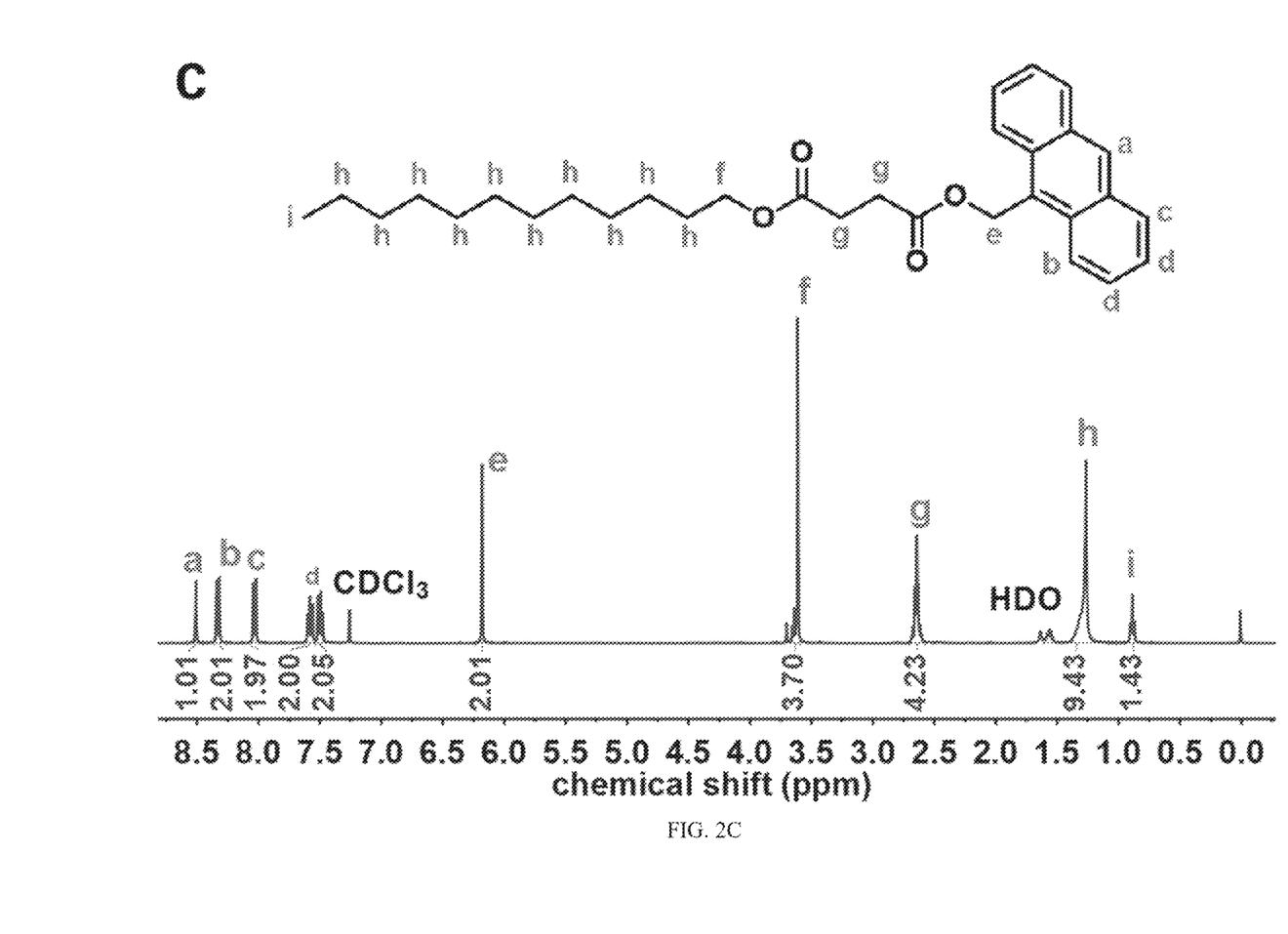
Figure 2D:
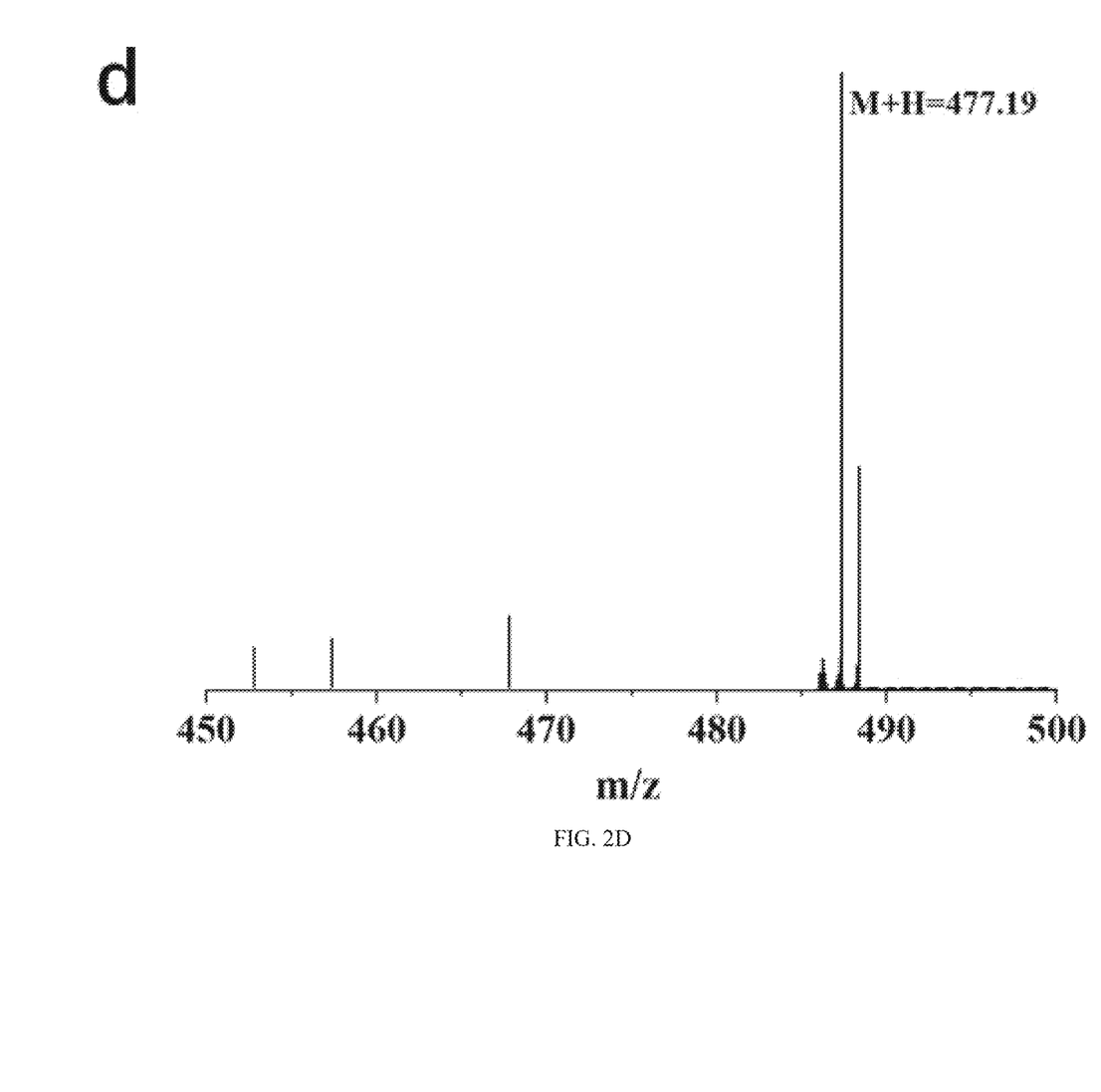

As shown in FIG. 1, the present invention provides a preparation method for the anthracene-based compound according to the foregoing technical solution, which includes the following steps:

mixing anthracene, N-methylformanilide, phosphorus oxychloride, and a first solvent for a formylation-condensation reaction to obtain 9-anthracenecarboxaldehyde;

mixing the 9-anthracenecarboxaldehyde, sodium borohydride, and a second solvent for a reduction reaction to obtain 9-anthracenemethanol;

mixing the 9-anthracenemethanol, succinic anhydride, 4-dimethylaminopyridine, and a third solvent for a substitution reaction to obtain 4-(anthracene-9-ylmethoxy)-4-oxobutyric acid; and mixing the 4-(anthracene-9-ylmethoxy)-4-oxobutyric acid, 1-ethyl(3-dimethylaminopropyl)-3-carbodiimide hydrochloride, 4-dimethylaminopyridine, a long-chain fatty alcohol, and a fourth solvent for an esterification reaction to obtain the anthracene-based compound;

wherein the long-chain fatty alcohol has 12-18 carbon atoms.

In the present invention, unless otherwise specified, the required raw materials or reagents for preparation are all commercially available products well known to those skilled in the art.

According to the present invention, anthracene, N-methylformanilide, phosphorus oxychloride, and a first solvent are mixed for a formylation-condensation reaction to obtain 9-anthracenecarboxaldehyde.

In the present invention, the anthracene is preferably commercially available or is obtained from coal tar; and the present invention preferably uses a method for separating anthracene from coal tar disclosed in Chinese Patent CN115141077B to extract anthracene.

In the present invention, the molar ratio of the anthracene to the N-methylformanilide to the phosphorus oxychloride is preferably 1:2:2 to 1:4:4, and more preferably 1:3:3.

In the present invention, the first solvent is preferably o-dichlorobenzene; and the volume ratio of the N-methylformanilide to the first solvent is preferably 10:1 to 5:1, and more preferably 7-9:1.

According to the present invention, the anthracene, N-methylformanilide, and the phosphorus oxychloride are preferably mixed, the first solvent is added, and the mixed liquid is heated and stirred in an oil bath to the reaction temperature, wherein the reaction temperature is kept for 30-60 min, preferably 50 min. The anthracene is dissolved to form a dark red solution, hydrochloric acid is precipitated, and the formylation-condensation reaction is performed.

In the present invention, the formylation-condensation reaction is performed at a temperature of preferably 90-100° C., and more preferably 95-98° C. The formylation-condensation reaction is performed for preferably 2-8 h, and more preferably 3-6 h.

After the formylation-condensation reaction is completed, dichloromethane is added into the obtained product, and the product is washed several times by using a saturated sodium chloride solution. The organic phase is dried over magnesium sulfate and filtered, the solvent is evaporated, and the 9-anthracenecarboxaldehyde is obtained. The present invention has no particular limitation on the washing, drying, filtering, and solvent evaporation, which are performed based on processes well known in the art.

According to the present invention, 9-anthracenemethanol is obtained by mixing the 9-anthracenecarboxaldehyde, sodium borohydride, and a second solvent for a reduction reaction.

In the present invention, the molar ratio of the 9-anthracenecarboxaldehyde to the sodium borohydride is preferably 1:2 to 1:3. The second solvent is preferably ethanol. The present invention has no particular limitation on the amount of the second solvent used, as long as the reaction proceeds smoothly.

According to the present invention, sodium borohydride is preferably added into a solvent containing 9-anthracenecarboxaldehyde at 0° C., and the mixture is subjected to a reduction reaction under stirring; wherein the reduction reaction is performed at a temperature of preferably 25° C. for preferably 4-8 h.

After the reduction reaction is completed, concentrated hydrochloric acid is preferably dropwise added into the obtained product to decompose unreacted sodium borohydride, and then water is added to adjust to neutrality. Dichloromethane is added to separate an organic layer, and the organic layer is washed by using a saturated sodium chloride solution several times, dried over anhydrous magnesium sulfate, and filtered. The filtrate is distilled under reduced pressure, and an obtained crude product is recrystallized by using ethanol to obtain the 9-anthracenemethanol.

In the present invention, the mass concentration of the concentrated hydrochloric acid is preferably 12 M; the volume ratio of the concentrated hydrochloric acid to the second solvent is preferably 1:15 to 1:10, and more preferably 1:12.5; the volume ratio of the dichloromethane to the saturated sodium chloride solution is preferably 1:2 to 1:6, and more preferably 1: (3-4.8); the number of washing with saturated sodium chloride solution is preferably 2 to 6 times, more preferably 3 to 4 times; and the number of recrystallization is preferably 2 to 5 times, and more preferably 3 times.

According to the present invention, 4-(anthracene-9-ylmethoxy)-4-oxobutyric acid is obtained by mixing the 9-anthracenemethanol, succinic anhydride, 4-dimethylaminopyridine, and a third solvent for a substitution reaction.

In the present invention, the molar ratio of the 9-anthracenemethanol to the 4-dimethylaminopyridine to the succinic anhydride is preferably 1:1:4 to 1:2:6, and more preferably 1:1:5 to 1:2:6.

In the present invention, the third solvent preferably includes dichloromethane and pyridine; and the volume ratio of the dichloromethane to the pyridine is preferably 1:1 to 3:1, and more preferably 2:1. The present invention has no particular limitation on the amount of the third solvent, as long as the reaction proceeds smoothly.

According to the present invention, the 9-anthracenemethanol, the 4-dimethylaminopyridine, and the succinic anhydride are preferably mixed, and a third solvent is added to dissolve the mixture; and the substitution reaction is performed under stirring.

In the present invention, the substitution reaction is performed at a temperature of preferably 25° C. for preferably 24-48 h, and more preferably 36 h.

After the substitution reaction is completed, the obtained mixture is poured into an ice/water mixture and heated to room temperature; dichloromethane is added to separate the organic layer, which is then extracted several times with a saturated sodium chloride solution. The collected organic layer is dried over anhydrous magnesium sulfate, filtered, and concentrated in vacuum to obtain 4-(anthracen-9-ylmethoxy)-4-oxobutanoic acid. In the present invention, the volume ratio of the dichloromethane to the saturated sodium chloride solution is preferably 1:2 to 1:6, and more preferably 1:2.5. The number of extraction with the saturated sodium chloride solution is preferably 2-5 times, and more preferably 4 times.

According to the present invention, the anthracene-based compound is obtained by mixing the 4-(anthracene-9-ylmethoxy)-4-oxobutyric acid, 1-ethyl(3-dimethylaminopropyl)-3-carbodiimide hydrochloride, 4-dimethylaminopyridine, a long-chain fatty alcohol, and a fourth solvent for an esterification reaction.

In the present invention, the molar ratio of the 4-(anthracene-9-ylmethoxy)-4-oxobutyric acid to the 1-ethyl(3-dimethylaminopropyl)-3-carbodiimide hydrochloride to the 4-dimethylaminopyridine to the long-chain fatty alcohol is preferably 1:4:2:1 to 1:6:5:3, and more preferably 1:5:3:3. The number of carbon atoms of the long-chain fatty alcohol is 12-18, preferably 12, 15 or 18.

In the present invention, the fourth solvent is preferably chloroform. The present invention has no particular limitation on the amount of the fourth solvent used, as long as the reaction proceeds smoothly.

According to the present invention, the 4-(anthracene-9-ylmethoxy)-4-oxobutyric acid, 1-ethyl(3-dimethylaminopropyl)-3-carbodiimide hydrochloride (EDAC), and the 4-dimethylaminopyridine (DMAP) are preferably mixed, a fourth solvent is added, and magnetic stirring is performed to dissolve the solids. Then a long-chain fatty alcohol is added, and the obtained mixture is subjected to an esterification reaction under continuous stirring conditions.

In the present invention, the esterification reaction is performed at a temperature of preferably 25° C. for preferably 24-48 h, and more preferably 36 h.

After the esterification reaction is completed, 5 wt % diluted aqueous hydrochloric acid solution is preferably added to the obtained product system, and the combined organic layer is extracted with saturated aqueous sodium bicarbonate solution. The obtained organic layer is dried over magnesium sulfate, filtered under reduced pressure, concentrated by rotary evaporation, and purified by column chromatography to obtain an anthracene-based compound.

In the present invention, the volume ratio of the dilute aqueous hydrochloric acid solution to the fourth solvent is preferably 1:3 to 1:6, and more preferably 1: (3.75-5); and the number of extraction with the saturated aqueous sodium bicarbonate solution is preferably 3-5 times. The developing solvent used for column chromatography purification is preferably ethyl acetate and n-hexane, wherein the volume ratio of the ethyl acetate to the n-hexane is preferably 1:1 to 1:3, and more preferably 1:2.

The present invention provides use of the anthracene-based compound according to the foregoing technical solution or an anthracene-based compound prepared by the preparation method according to the foregoing technical solution as a solar thermal fuel.

The present invention has no particular limitation on the use method, and the anthracene-based compound can be directly used as a solar thermal fuel.

The technical solutions provided by the present invention will be described in detail below with reference to examples, which, however, should not be construed as limiting the scope of the present invention.

Example 1

1) Anthracene (5.00 g, 28.00 mmol), N-methylformanilide (6.3 mL, 7.58 g, 56.00 mmol), and phosphorus oxychloride (8.56 g, 56.00 mmol) were placed in a 100 mL round-bottom flask containing 0.7 mL o-dichlorobenzene and then heated in an oil bath at 1500 r/min with stirring to 95° C. for 30 min; wherein the anthracene was dissolved to form a dark red solution, hydrochloric acid was precipitated, and heating was continuously performed for 3 h. After the reaction was completed, 25 mL of dichloromethane was added, and the mixture was washed 3 times by using 50 mL of saturated sodium chloride solution; the organic phase was dried over magnesium sulfate at room temperature for 12 h and filtered; and the solvent was evaporated at 30° C. for 1 h to obtain 9-anthracenecarboxaldehyde. Sodium borohydride (0.34 g, 9.60 mmol) was added to a solution of the 9-anthracenecarboxaldehyde (1.00 g, 4.80 mmol) in ethanol (50 mL) at 0° C., the reaction mixture was stirred at 25° C. for 4 h at 1500 r/min, 5 mL of concentrated hydrochloric acid (with a concentration of 12 M) was dripped, and then water was added to adjust to be neutrality. 25 mL of dichloromethane was added to separate an organic layer, the organic layer was washed 3 times by using 50 mL of saturated sodium chloride solution, dried with 150 g of anhydrous magnesium sulfate at 45° C. for 12 h, filtered, and distilled under reduced pressure (0.02 MPa, 30° C., and 1 h). The obtained crude product was recrystallized for 12 h by using 50 mL of ethanol at 4° C., and recrystallization was performed 2 times to obtain 9-anthracenemethanol in light yellow.

2) A mixture of 9-anthracenemethanol (2.08 g, 10.00 mmol), 4-dimethylaminopyridine (1.23 g, 10.01 mmol), and succinic anhydride (4.00 g, 40.02 mmol) was placed in a 250 mL round-bottom flask, a mixed solution of 50 mL of anhydrous dichloromethane and 50 mL of anhydrous pyridine was then added, and the resulting mixed solution was stirred at 1500 r/min at 25° C. for 24 h. After the reaction was completed, the mixture solution was poured into 200 mL of ice/water mixture and heated to room temperature, 50 mL of dichloromethane was added to separate the organic layer, then the organic layer was washed 3 times with 100 mL of saturated sodium chloride solution, and the collected organic layer was dried over 150 g of anhydrous magnesium sulfate at room temperature for 12 h, filtered, and concentrated under vacuum at 0.02 MPa at 30° C. for 1 h to obtain 4-(anthracene-9-ylmethoxy)-4-oxobutyric acid as an intermediate.

3) The 4-(anthracene-9-ylmethoxy)-4-oxobutyric acid (1.48 g, 4.80 mmol), 1-ethyl(3-dimethylaminopropyl)-3-carbodiimide hydrochloride (3.67 g, 19.20 mmol), and p-dimethylaminopyridine (1.17 g, 9.60 mmol) were placed sequentially in a 250 mL single-necked round-bottom flask, 150 mL of chloroform was added, and the mixture was dissolved with magnetic stirring at 1500 r/min. The n-dodecanol (0.89 g, 4.80 mmol) was added to the round-bottom flask and the mixture was stirred continuously at 25° C. for 24 h. After the reaction was completed, 50 mL of a 5 wt % dilute aqueous hydrochloric acid solution was added, the mixture was washed 3 times with 50 mL of a saturated aqueous sodium bicarbonate solution, and the resulting organic layer was dried over 150 g of magnesium sulfate, filtered under reduced pressure of 0.02 MPa, concentrated for 1 h by rotary evaporation at 45° C., and purified by column chromatography (ethyl acetate to n-hexane in a volume ratio=1:2) to obtain the anthracene-based compound.

Example 2

1) Anthracene (5.00 g, 28.00 mmol), N-methylformanilide (9.45 mL, 11.34 g, 84.00 mmol), and phosphorus oxychloride (12.85 g, 84.00 mmol) were placed in a 100 mL round-bottom flask containing 1.35 mL o-dichlorobenzene and then heated in an oil bath at 1500 r/min with stirring to 98° C. for 50 min; wherein the anthracene was dissolved to form a dark red solution, hydrochloric acid was precipitated, and heating was continuously performed for 6 h. After the reaction was completed, 25 mL of dichloromethane was added, and the mixture was washed 4 times by using 75 mL of saturated sodium chloride solution; the organic phase was dried over magnesium sulfate at room temperature for 12 h and filtered; and the solvent was evaporated at 30° C. for 1 h to obtain 9-anthracenecarboxaldehyde. Sodium borohydride (0.34 g, 9.60 mmol) was added to a solution of the 9-anthracenecarboxaldehyde (1.00 g, 4.80 mmol) in ethanol (50 mL) at 0° C., the reaction mixture was stirred at 25° C. for 4 h at 1500 r/min, 4 mL of concentrated hydrochloric acid (with a concentration of 12 M) was dripped, and then water was added to adjust to be neutrality. After the reaction was completed, 25 mL of dichloromethane was added to separate an organic layer, the organic layer was washed 4 times by using 75 mL of saturated sodium chloride solution, dried with 150 g of anhydrous magnesium sulfate at 45° C. for 12 h, filtered, and distilled under reduced pressure (0.02 MPa, 30° C., and 1 h). The obtained crude product was recrystallized for 12 h by using 50 mL of ethanol at 4° C., and recrystallization was performed 3 times to obtain 9-anthracenemethanol in light yellow.

2) A mixture of 9-anthracenemethanol (2.08 g, 10.00 mmol), 4-dimethylaminopyridine (2.44 g, 20.01 mmol), and succinic anhydride (5.00 g, 50.02 mmol) was placed in a 250 mL round-bottom flask, a mixed solution of 100 mL of anhydrous dichloromethane and 100 mL of anhydrous pyridine was then added, and the resulting mixed solution was stirred at 1500 r/min at 25° C. for 36 h. After the reaction was completed, the mixture solution was poured into 200 mL of ice/water mixture and heated to room temperature, 50 mL of dichloromethane was added to separate the organic layer, then the organic layer was washed 4 times with 250 mL of saturated sodium chloride solution, and the collected organic layer was dried over 150 g of anhydrous magnesium sulfate at room temperature for 12 h, filtered, and concentrated under vacuum at 0.02 MPa at 30° C. for 1 h to obtain 4-(anthracene-9-ylmethoxy)-4-oxobutyric acid as an intermediate.

3) The 4-(anthracene-9-ylmethoxy)-4-oxobutyric acid (1.48 g, 4.80 mmol), 1-ethyl(3-dimethylaminopropyl)-3-carbodiimide hydrochloride (3.67 g, 19.20 mmol), and p-dimethylaminopyridine (1.17 g, 9.60 mmol) were placed sequentially in a 250 mL single-necked round-bottom flask, 150 mL of chloroform was added, and the mixture was dissolved with magnetic stirring at 1500 r/min. The n-dodecanol (1.78 g, 9.60 mmol) was added to the round-bottom flask and the mixture was stirred continuously at 25° C. for 36 h. After the reaction was completed, 30 mL of a 5 wt % dilute aqueous hydrochloric acid solution was added, the mixture was washed 4 times with 50 mL of a saturated aqueous sodium bicarbonate solution, and the resulting organic layer was dried over 150 g of magnesium sulfate, filtered under reduced pressure of 0.02 MPa, concentrated for 1 h by rotary evaporation at 45° C., and purified by column chromatography (ethyl acetate to n-hexane in a volume ratio=1:3) to obtain the anthracene-based compound.

Example 3

1) Anthracene (2.50 g, 14.00 mmol), N-methylformanilide (6.3 mL, 7.56 g, 56.00 mmol), and phosphorus oxychloride (8.57 g, 56.00 mmol) were placed in a 100 mL round-bottom flask containing 1.20 mL o-dichlorobenzene and then heated in an oil bath at 1500 r/min with stirring to 100° C. for 60 min; wherein the anthracene was dissolved to form a dark red solution, hydrochloric acid was precipitated, and heating was continuously performed for 8 h. After the reaction was completed, 25 mL of dichloromethane was added, and the mixture was washed 5 times by using 150 mL of saturated sodium chloride solution; the organic phase was dried over magnesium sulfate at room temperature for 12 h and filtered; and the solvent was evaporated at 30° C. for 1 h to obtain 9-anthracenecarboxaldehyde. Sodium borohydride (0.51 g, 14.40 mmol) was added to a solution of the 9-anthracenecarboxaldehyde (1.00 g, 4.80 mmol) in ethanol (50 mL) at 0° C., the reaction mixture was stirred at 25° C. for 8 h at 1500 r/min, 5 mL of concentrated hydrochloric acid (with a concentration of 12 M) was dripped, and then water was added to adjust to be neutrality. After the reaction was completed, 25 mL of dichloromethane was added to separate an organic layer, the organic layer was washed 5 times by using saturated sodium chloride solution (120 mL), dried with 150 g of anhydrous magnesium sulfate at 45° C. for 12 h, filtered, and distilled under reduced pressure (0.02 MPa, 30° C., and 1 h). The obtained crude product was recrystallized for 12 h by using 50 mL of ethanol at 4° C., and recrystallization was performed 3 times to obtain 9-anthracenemethanol in light yellow.

2) A mixture of 9-anthracenemethanol (2.08 g, 10.00 mmol), 4-dimethylaminopyridine (2.44 g, 20.01 mmol), and succinic anhydride (6.00 g, 60.02 mmol) was placed in a 250 mL round-bottom flask, a mixed solution of 150 mL of anhydrous dichloromethane and 150 mL of anhydrous pyridine was then added, and the resulting mixed solution was stirred at 1500 r/min at 25° C. for 48 h. After the reaction was completed, the mixture solution was poured into 200 mL of ice/water mixture and heated to room temperature, 50 mL of dichloromethane was added to separate the organic layer, then the organic layer was washed 5 times with 300 mL of saturated sodium chloride solution, and the collected organic layer was dried over 150 g of anhydrous magnesium sulfate at room temperature for 12 h, filtered, and concentrated under vacuum at 0.02 MPa at 30° C. for 1 h to obtain 4-(anthracene-9-ylmethoxy)-4-oxobutyric acid as an intermediate.

3) The 4-(anthracene-9-ylmethoxy)-4-oxobutyric acid (1.48 g, 4.80 mmol), 1-ethyl(3-dimethylaminopropyl)-3-carbodiimide hydrochloride (4.58 g, 24.00 mmol), and 4-dimethylaminopyridine (1.75 g, 14.40 mmol) were placed sequentially in a 250 mL single-necked round-bottom flask, 150 mL of chloroform was added, and the mixture was dissolved with magnetic stirring at 1500 r/min. The n-dodecanol (2.68 g, 14.40 mmol) was added to the round-bottom flask and the mixture was stirred continuously at 25° C. for 48 h. After the reaction was completed, 40 mL of a 5 wt % dilute aqueous hydrochloric acid solution was added, the mixture was washed 5 times with 50 mL of a saturated aqueous sodium bicarbonate solution, and the resulting organic layer was dried over 150 g of magnesium sulfate, filtered under reduced pressure of 0.02 MPa, concentrated for 1 h by rotary evaporation at 45° C., and purified by column chromatography (ethyl acetate to n-hexane in a volume ratio=1:2) to obtain the anthracene-based compound.

Characterization and Performance Testing

FIGS. 2A-2D are proton nuclear magnetic resonance (NMR) spectrums (deuterated chloroform) of 9-anthracenemethanol (FIG. 2A), the intermediate 4-(anthracen-9-ylmethoxy)-4-oxobutanoic acid (FIG. 2B) and the anthracene-based compound (FIG. 2C) and a mass spectrum of the anthracene-based compound (FIG. 2D) prepared in Example 1. It can be seen from FIGS. 2A-2D that the product 9-anthracenemethanol, the intermediate 4-(anthracen-9-ylmethoxy)-4-oxobutanoic acid and the target anthracene-based compound have all been successfully synthesized.

Figure 3A:
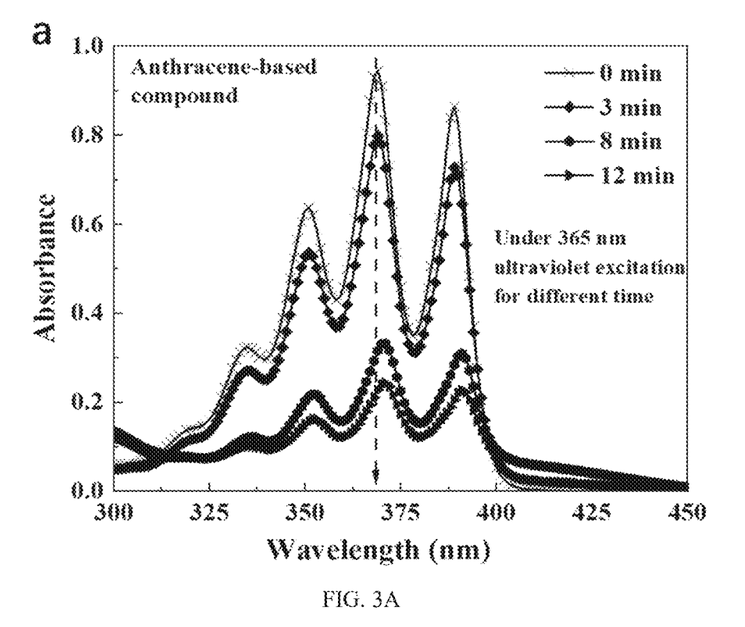
FIGS. 3A-3C are diagrams of the UV-visible absorption spectra of the anthracene-based compound in Example 1 after irradiation with 365 nm UV (FIG. 3A) and 254 nm UV (FIG. 3B) (at an irradiation power of 10 mW/cm²) for different times, and a schematic diagram of the photodimerization/depolymerization of the anthracene-based compound under alternating irradiation of 365 nm and 254 nm UV (FIG. 3C)
Figure 3B:
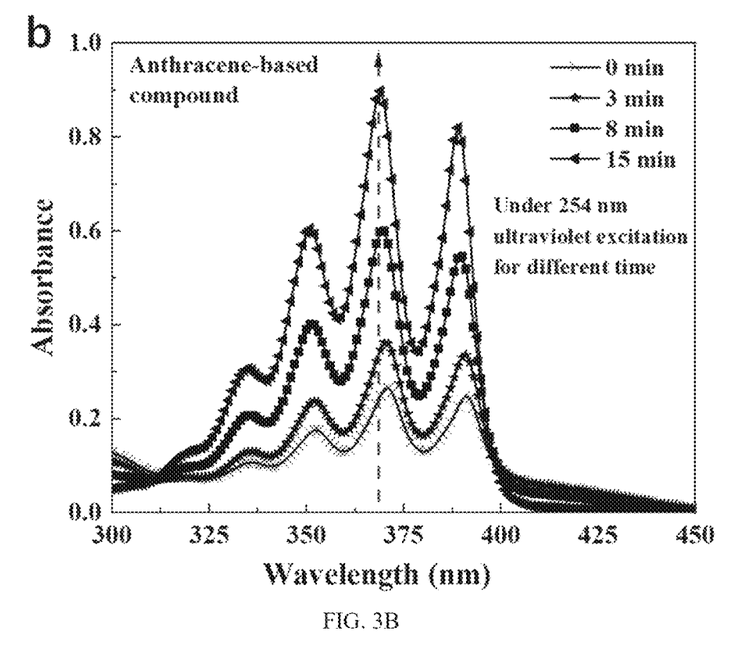
Figure 3C:
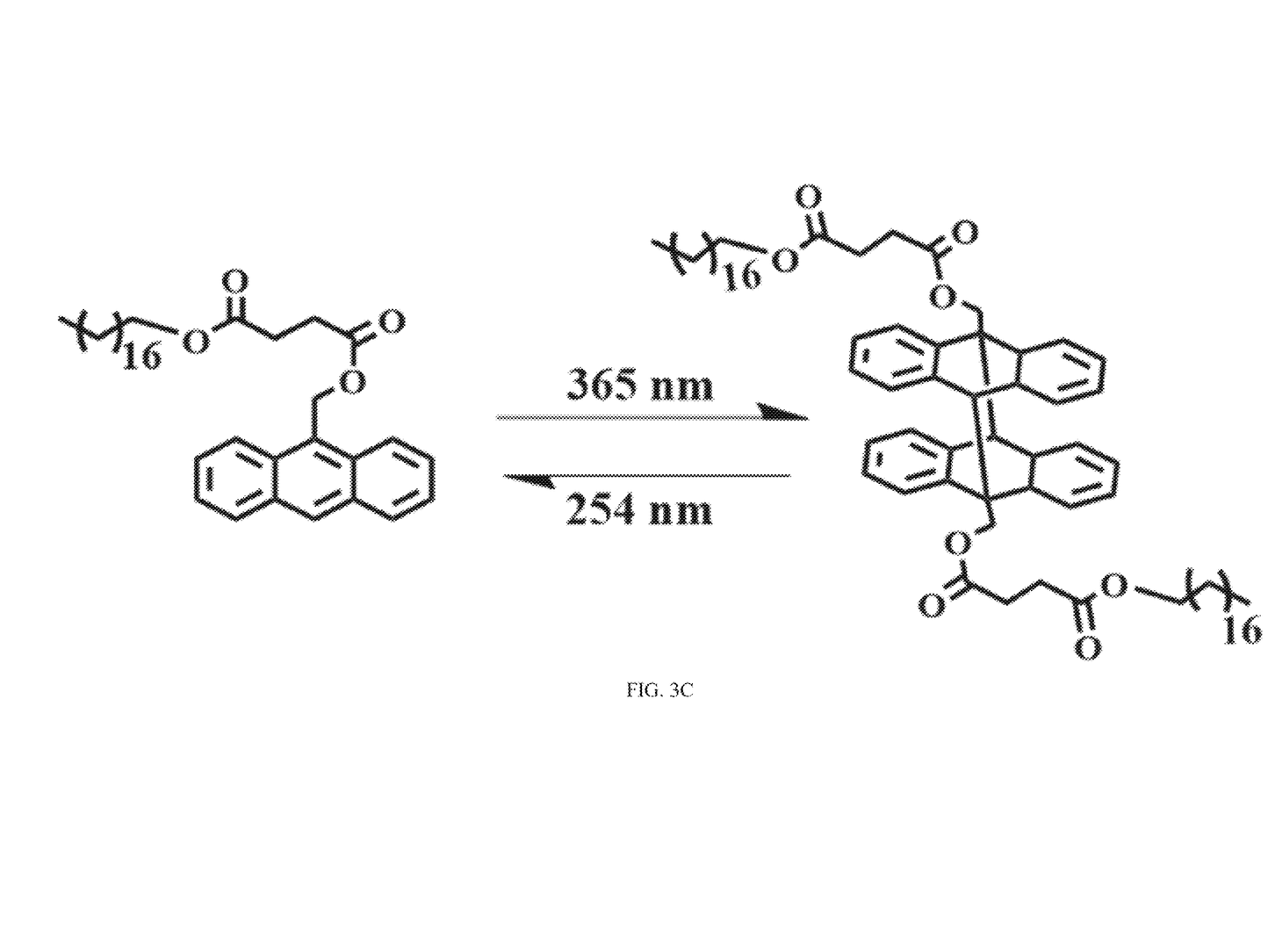

FIGS. 3A-3C are diagrams of the UV-visible absorption spectra of the anthracene-based compound in Example 1 after irradiation with 365 nm UV (FIG. 3A) and 254 nm UV (FIG. 3B) (a methanol solution, 1 M, at an irradiation power of 10 mW/cm$^2$) for different times, and a schematic diagram of the photodimerization/depolymerization of the anthracene-based compound under alternating irradiation of 365 nm and 254 nm UV (FIG. 3C). It can be seen from FIGS. 3A-3C that the anthracene-based compound is effective for reversible photodimerization/depolymerization reactions under ultraviolet irradiation.

Figure 4:
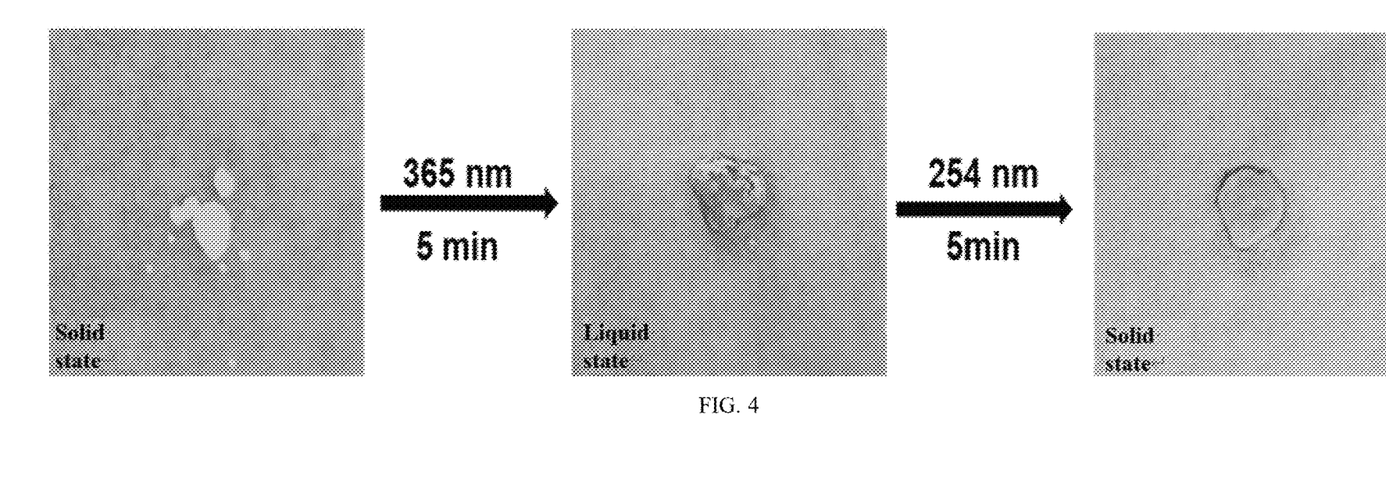
FIG. 4 is an optical photograph of photoinduced reversible solid-to-liquid transition of the anthracene-based compound prepared in Example 2 under alternating ultraviolet excitation (at an illumination power of 50 mW/cm²)

FIG. 4 is an optical photograph of photoinduced reversible solid-to-liquid transition of the anthracene-based compound prepared in Example 2 under alternating ultraviolet excitation (at an illumination power of 50 mW/cm$^2$). It can be seen from FIG. 4 that the prepared anthracene-based compound can achieve reversible solid-liquid phase transition under ultraviolet irradiation.

Figure 5A:
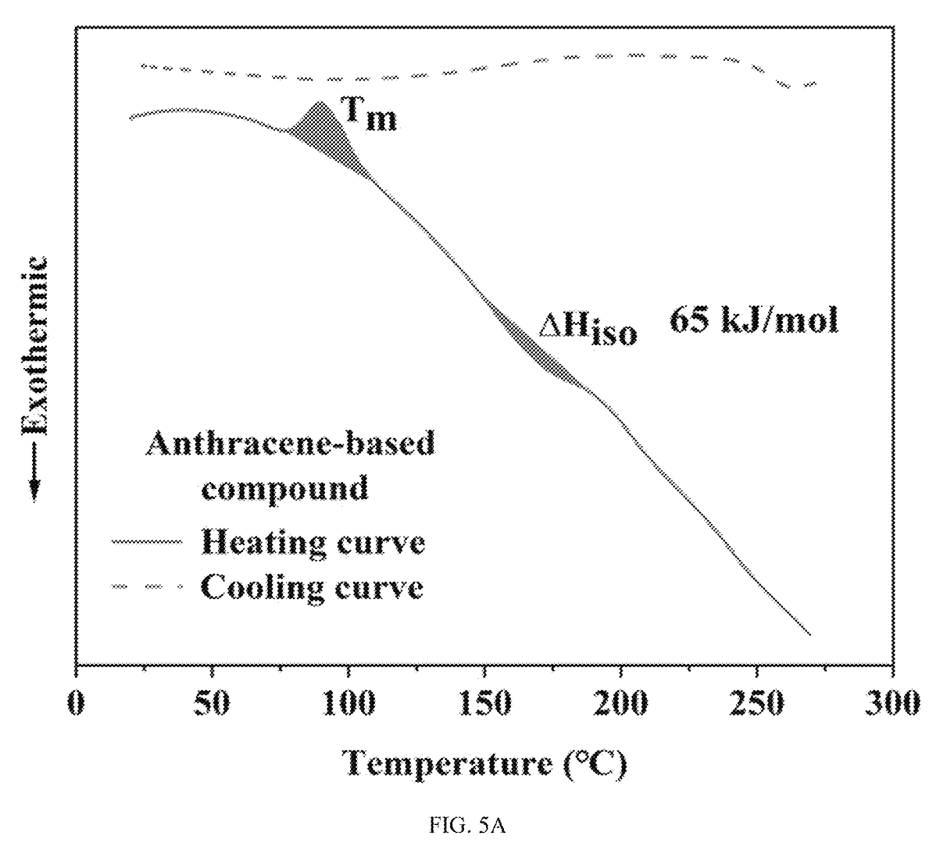
FIGS. 5A-5B show (FIG. 5A) a storage energy density test curve and (FIG. 5B) a reversion half-life curve of the anthracene-based compound in Example 3.
Figure 5B:
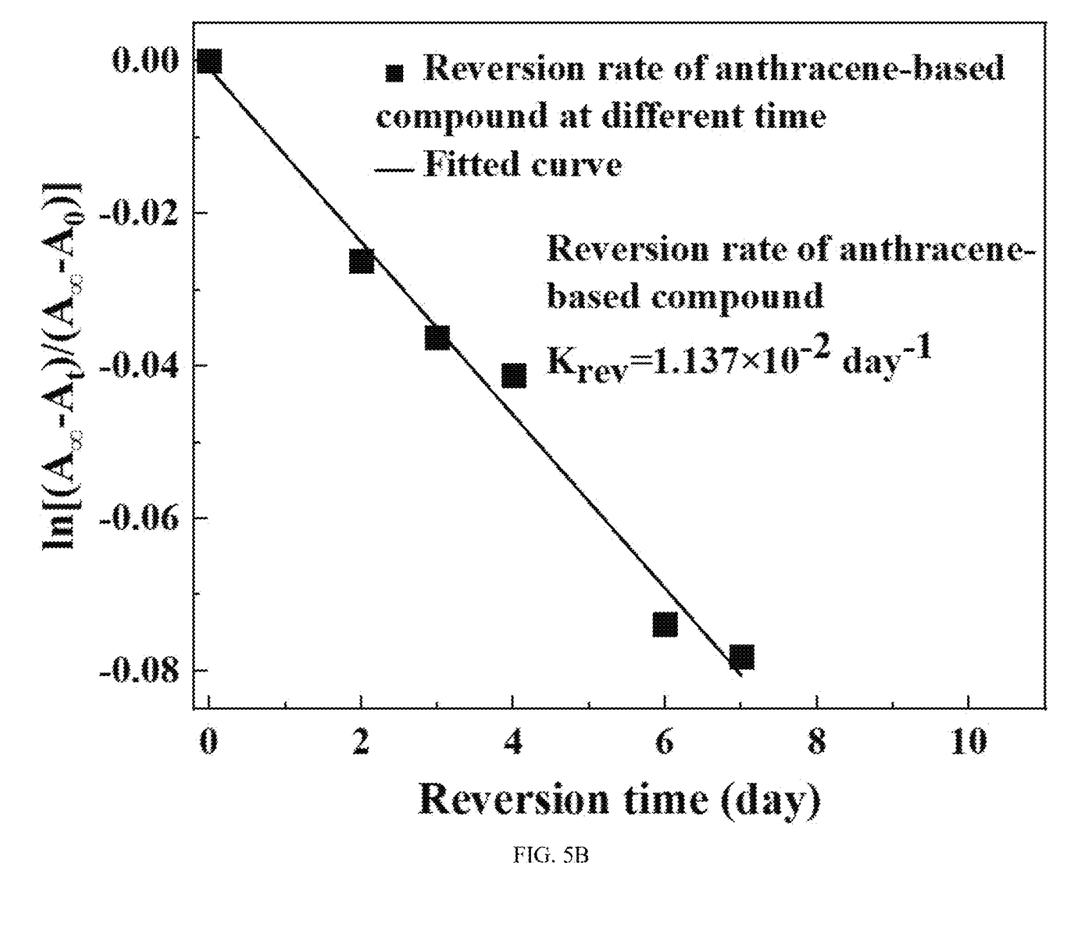

FIGS. 5A-5B show (FIG. 5A) a storage energy density test curve and (FIG. 5B) a reversion half-life curve of the anthracene-based compound in Example 3. It can be calculated from FIGS. 5A-5B that the energy density of the anthracene-based compound is 65 KJ/mol, and the energy storage time is as long as 60 days.

The above descriptions are only preferred embodiments of the present invention. It should be noted that those of ordinary skill in the art can also make several improvements and modifications without departing from the principle of

What is claimed is:

1. An anthracene-based compound, wherein a structure of the anthracene-based compound is represented by a formula 1:

formula 1 in the formula 1, n=10 to 16.

2. The anthracene-based compound according to claim 1, wherein n=10, 13, or 16.

3. A preparation method for the anthracene-based compound according to claim 1, comprising the following steps:
mixing anthracene, N-methylformanilide, phosphorus oxychloride, and a first solvent for a formylation-condensation reaction to obtain 9-anthracenecarboxaldehyde;
mixing the 9-anthracenecarboxaldehyde, sodium borohydride, and a second solvent for a reduction reaction to obtain 9-anthracenemethanol;
mixing the 9-anthracenemethanol, succinic anhydride, 4-dimethylaminopyridine, and a third solvent for a substitution reaction to obtain 4-(anthracene-9-ylmethoxy)-4-oxobutyric acid; and
mixing the 4-(anthracene-9-ylmethoxy)-4-oxobutyric acid, 1-ethyl(3-dimethylaminopropyl)-3-carbodiimide hydrochloride, 4-dimethylaminopyridine, a long-chain fatty alcohol, and a fourth solvent for an esterification reaction to obtain the anthracene-based compound;
wherein the long-chain fatty alcohol has 12-18 carbon atoms.

4. The preparation method according to claim 3, wherein the anthracene is obtained by a separation of a coal tar.

5. The preparation method according to claim 3, wherein a molar ratio of the anthracene to the N-methylformanilide to the phosphorus oxychloride is 1:2:2 to 1:4:4; a volume ratio of the N-methylformanilide to the first solvent is 10:1 to 5:1; and
the formylation-condensation reaction is performed at a temperature of 90-100° C. for 2-8 h.

6. The preparation method according to claim 3, wherein a molar ratio of the 9-anthracenecarboxaldehyde to the sodium borohydride is 1:2 to 1:3; and the reduction reaction is performed at a temperature of 25° C. for 4-8 h.

7. The preparation method according to claim 3, wherein the third solvent comprises dichloromethane and pyridine; and a volume ratio of the dichloromethane to the pyridine is 1:1 to 3:1.

8. The preparation method according to claim 3, wherein a molar ratio of the 9-anthracenemethanol to the succinic anhydride to the 4-dimethylaminopyridine is 1:1:4 to 1:2:6; and
the substitution reaction is performed at a temperature of 25° C. for 24-48 h.

9. The preparation method according to claim 3, wherein a molar ratio of the 4-(anthracene-9-ylmethoxy)-4-oxobutyric acid to the 1-ethyl(3-dimethylaminopropyl)-3-carbodiimide hydrochloride to the 4-dimethylaminopyridine to the long-chain fatty alcohol is 1:4:2:1 to 1:6:5:3; and
the esterification reaction is performed at a temperature of 25° C. for 24-48 h.

10. A method of using an anthracene-based compound according to claim 1 as a solar thermal fuel.

11. The preparation method according to claim 3, wherein in the anthracene-based compound, n=10, 13, or 16.

12. The preparation method according to claim 7, wherein a molar ratio of the 9-anthracenemethanol to the succinic anhydride to the 4-dimethylaminopyridine is 1:1:4 to 1:2:6; and
the substitution reaction is performed at a temperature of 25° C. for 24-48 h.

13. The method according to claim 10, wherein in the anthracene-based compound, n=10, 13, or 16.

14. The method according to claim 10, wherein a preparation method for the anthracene-based compound comprises the following steps:
mixing anthracene, N-methylformanilide, phosphorus oxychloride, and a first solvent for a formylation-condensation reaction to obtain 9-anthracenecarboxaldehyde;
mixing the 9-anthracenecarboxaldehyde, sodium borohydride, and a second solvent for a reduction reaction to obtain 9-anthracenemethanol;
mixing the 9-anthracenemethanol, succinic anhydride, 4-dimethylaminopyridine, and a third solvent for a substitution reaction to obtain 4-(anthracene-9-ylmethoxy)-4-oxobutyric acid; and
mixing the 4-(anthracene-9-ylmethoxy)-4-oxobutyric acid, 1-ethyl(3-dimethylaminopropyl)-3-carbodiimide hydrochloride, 4-dimethylaminopyridine, a long-chain fatty alcohol, and a fourth solvent for an esterification reaction to obtain the anthracene-based compound;
wherein the long-chain fatty alcohol has 12-18 carbon atoms.

15. The method according to claim 14, wherein in the preparation method for the anthracene-based compound, the anthracene is obtained by a separation of a coal tar.

16. The method according to claim 14, wherein in the preparation method for the anthracene-based compound, a molar ratio of the anthracene to the N-methylformanilide to the phosphorus oxychloride is 1:2:2 to 1:4:4; a volume ratio of the N-methylformanilide to the first solvent is 10:1 to 5:1; and
the formylation-condensation reaction is performed at a temperature of 90-100° C. for 2-8 h.

17. The method according to claim 14, wherein in the preparation method for the anthracene-based compound, a molar ratio of the 9-anthracenecarboxaldehyde to the sodium borohydride is 1:2 to 1:3; and the reduction reaction is performed at a temperature of 25° C. for 4-8 h.

18. The method according to claim 14, wherein in the preparation method for the anthracene-based compound, the third solvent comprises dichloromethane and pyridine; and a volume ratio of the dichloromethane to the pyridine is 1:1 to 3:1.

19. The method according to claim 14, wherein in the preparation method for the anthracene-based compound, a molar ratio of the 9-anthracenemethanol to the succinic anhydride to the 4-dimethylaminopyridine is 1:1:4 to 1:2:6; and the substitution reaction is performed at a temperature of 25° C. for 24-48 h.

20. The method according to claim 14, wherein in the preparation method for the anthracene-based compound, a molar ratio of the 4-(anthracene-9-ylmethoxy)-4-oxobutyric acid to the 1-ethyl(3-dimethylaminopropyl)-3-carbodiimide hydrochloride to the 4-dimethylaminopyridine to the long-chain fatty alcohol is 1:4:2:1 to 1:6:5:3; and the esterification reaction is performed at a temperature of 25° C. for 24-48 h.

* * * * *